United States Patent [19]

Schönafinger et al.

[11] Patent Number: 4,551,454

[45] Date of Patent: Nov. 5, 1985

[54] 3-(4-ALKOXYCARBONYLPIPERAZIN-1-YL)-SYDNONIMINES, A PROCESS FOR THEIR PREPARATION AND USE

[75] Inventors: Karl Schönafinger, Uehlfeld; Rudi Beyerle, Frankfurt am Main; Helmut Bohn; Melitta Just, both of Schoöneck; Piero A. Martorana, Bad Homburg; Rolf-Eberhard Nitz, Frankfurt am Main, all of Fed. Rep. of Germany

[73] Assignee: Cassella Aktiengesellschaft, Fed. Rep. of Germany

[21] Appl. No.: 477,146

[22] Filed: May 6, 1983

Related U.S. Application Data

[62] Division of Ser. No. 350,366, Feb. 19, 1982, Pat. No. 4,436,743.

[30] Foreign Application Priority Data

Mar. 2, 1981 [DE] Fed. Rep. of Germany ....... 3107933

[51] Int. Cl.$^4$ .................... C07D 413/04; A61K 31/41
[52] U.S. Cl. ..................................... 514/252; 544/367
[58] Field of Search ................ 548/125; 424/269, 250; 544/367

[56] References Cited

U.S. PATENT DOCUMENTS

| | | | |
|---|---|---|---|
| 3,769,283 | 10/1973 | Masuda et al. | 544/367 |
| 3,833,580 | 9/1974 | Gotz et al. | 544/367 |
| 3,833,589 | 9/1974 | Simpson | 544/367 |
| 4,421,754 | 12/1983 | Hidaka et al. | 544/367 |
| 4,430,342 | 2/1984 | Hidaka et al. | 544/367 |
| 4,436,743 | 3/1984 | Schonafinger et al. | 544/367 |
| 4,452,797 | 6/1984 | Schonafinger et al. | 544/367 |

Primary Examiner—Donald G. Daus
Assistant Examiner—S. A. Gibson
Attorney, Agent, or Firm—Berman, Aisenberg & Platt

[57] ABSTRACT

Pharmacologically-active 3-aminosydnonimines (which are optionally substituted in the $N^6$-position) and their physiologically-acceptable acid-addition salts are compounded into standard dosage-form medicament compositions and are useful for prophylaxis for and treatment of cardiovascular-system disorders, such as high blood pressure and angina pectoris. The 3-aminosydnonimines are 3-[4-(lower alkoxy)carbonylpiperazin-1-yl]sydnonimines and 3-[N-(lower alkyl)-N-(tetrahydro-3-thienyl S,S-dioxide)]-sydnonimines.

25 Claims, No Drawings

3-(4-ALKOXYCARBONYLPIPERAZIN-1-YL)-SYDNONIMINES, A PROCESS FOR THEIR PREPARATION AND USE

CROSS-REFERENCE TO RELATED APPLICATION

The present application is a division of application Ser. No. 350,366, filed Feb. 19, 1982 now U.S. Pat. No. 4,436,743.

The invention relates to pharmacologically-active substituted 3-aminosydnonimines of the general formula I

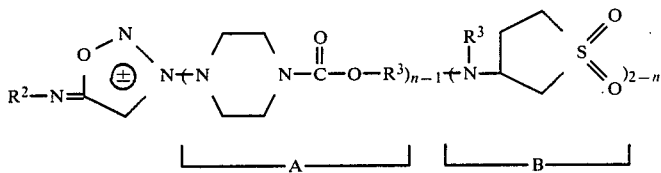

and their addition salts, wherein
$R^2$ is -H or -CO-$R^4$;

$R^3$ is methyl, ethyl, propyl or isopropyl;
$R^4$ is aliphatic hydrocarbyl with from 1 to 4 carbon atoms and optionally substituted by alkoxy with from 1 to 3 carbon atoms, cycloaliphatic hydrocarbyl with from 5 to 7 ring carbon atoms, bicycloaliphatic hydrocarbyl with from 7 to 14 ring carbon atoms, tricycloaliphatic hydrocarbyl with from 7 to 16 ring carbon atoms, alkoxy with from 1 to 6 carbon atoms, carbocyclic aryloxy with from 6 to 12 ring carbon atoms, alkoxycarbonyl with from 2 to 7 carbon atoms, carbocyclic aryl with from 6 to 12 ring carbon atoms or such aryl with from 1 to 3 substitutents each of which is a member selected from the group consisting of halo, alkyl with from 1 to 3 carbon atoms, alkoxy with from 1 to 3 carbon atoms and nitro, and at most 2 of which are nitro; and
n is a positive whole number of at most 2.

The invention furthermore relates to a process for the preparation of the compounds according to the invention and to their use.

Aliphatic radicals, alkoxy radicals or alkoxycarbonyl radicals $R^4$ can be straight-chain or branched. Possible aliphatic radicals $R^4$ are, in particular, alkyl radicals with 1 to 4 C atoms. The methoxymethyl radical may be mentioned, in particular, as an aliphatic radical $R^4$ which is substituted by alkoxy with 1 to 3 C atoms. Possible cycloaliphatic radicals $R^4$ are, above all, cycloalkyl radicals with 5 to 7 C atoms, in particular cyclopentyl and, preferably, cyclohexyl. A possible bicycloaliphatic radical $R^4$ is, in particular, 2,6,6-trimethylbicyclo[3.1.1]heptan-3-yl (=pinyl). A possible tricycloaliphatic radical $R^4$ is, in particular, tricyclo[3.3.1.1$^{3,7}$[dec-1-yl (=adamantyl). Possible alkoxy radicals $R^4$ are, in particular, the methoxy and ethyoxy radicals. A possible alkoxycarbonyl radical $R^4$ is, in particular, the ethoxycarbonyl radical. Aryl radicals $R^4$ which may be mentioned are, for example, α- or β-naphthyl radicals, but in particular the phenyl radical. Aryloxy radicals $R^4$ which may be mentioned are, for example, α- or β-naphthoxy radicals, but in particular the phenoxy radical. The aryl radicals $R^4$ can be monosubstituted, disubstituted or trisubstituted, but even in the case of trisubstitution, only at most 2 nitro groups may be present, such as, for example, 2-methyl-4,6-dinitrophenyl and 2-chloro-6-methyl-4-nitrophenyl. Possible halogen substituents for the aryl radicals are, for example, chlorine and bromine atoms. Substituted aryl radicals $R^4$ which may be mentioned are, in particular: methyl-phenyl (tolyl), nitro-phenyl and chloro-phenyl.

$R^3$ is preferably methyl or ethyl. $R^4$ is preferably methyl, ethyl, cyclohexyl, phenyl, 4-chloro-phenyl or 4-nitrophenyl. $R^1$ is A or B, preferably the radical

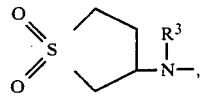

in particular where $R^3$ =methyl and especially in combination with $R^2$ =hydrogen.

The compounds of the general formula I can be prepared by a process in which compounds of the general formula II

are cyclised to give compounds of the general formula Ia

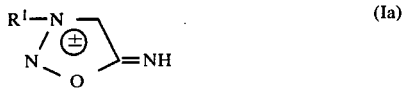

and, in the case where $R^2 = -COR^4$, the compounds of the formula Ia or their acid-addition salts are acylated with acylating agents which introduce the radical $-COR^4$, and, if desired, the compounds thus obtained are converted into acid-addition salts.

Cyclisation of the compounds II to give the compounds Ia is carried out in a suitable organic or inorganic solvent, for example water, an alkanol with 1 to 4 C atoms, a carboxylic acid alkyl ester, for example ethyl acetate, or a mixture of such solvents, such as water/methanol or, preferably, ethyl acetate/methanol, with the addition of a cyclising atent, usually at temperatures from 0° to 40° C., preferably at 0° to 20° C. Suitable cyclising agents are those which establish a pH value below 3 in aqueous solution, thus, for example, mineral acids, such as sulphuric acid, nitric acid, phosphoric acid or, preferably, hydrochloric acid, and also strong organic acids, such as trifluoroacetic acid. The cyclisation gives the corresponding acid-addition salt of the compound Ia. The compounds of the formula Ia are compounds according to the invention where $R^2$ is hydrogen.

Acylation of the compounds of the formula Ia to introduce the radical $R^2 = -COR^4$ can be carried out in a manner which is in itself known, using suitable acylating agents of the formula III

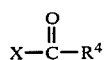 (III)

wherein X denotes, for example, halogen, in particular chlorine,

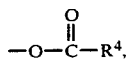

aryloxy, in particular tolyloxy, dinitrophenyloxy or nitrophenyloxy. The acylation is carried out in a suitable solvent, such as, for example, water, a polar organic solvent, such as dimethylformamide, dimethylsulphoxide or pyridine, a solvent mixture, such as, for example, water/methylene chloride, or in an excess of the acylating agent, advantageously whilst stirring and at temperatures from 0° C. to the boiling point of the solvent or acylating agent, preferably from 0° to 20° C. An acid-binding agent, such as, for example, pyridine, sodium bicarbonate or sodium acetate, is advantageously present during the acylation.

The substituted 3-amino-sydnonimines of the general formula I form acid-addition salts with inorganic or organic acids. Inorganic and organic acids are suitable for the formation of such acid-addition salts. Examples of suitable acids are hydrogen chloride, hydrogen bromide, naphthalenedisulphonic acids, in particular naphthalene-1,5-disulphonic acid, and phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. Pharmacologically acceptable acid-addition salts are preferred. The acid-addition salts can be prepared in the customary manner by combining the components, advantageously in a suitable solvent or diluent. In the synthesis of compounds of the formula Ia, the acid-addition salts are obtained. If desired, the free compounds of the general formula I or Ia can be obtained from the acid-addition salts in a known manner, that is to say by dissolving or suspending the salts in water, rendering the solution or suspension alkaline, for example with sodium hydroxide solution, and then isolating the free compounds.

All acid-addition salts are within the scope of this invention. Those which are pharmacologically acceptable are directly useful as hereinafter taught. Those which are not pharmacologically acceptable are readily converted by known and well-established conventional procedures either to their corresponding free bases or to pharmacologically-acceptable acid-addition salts. All pharmacologically-acceptable acid-addition salts of the pharmacologically-active substituted 3-aminosydnonimines of formula I are useful for treating or preventing cardiovascular system disorders, such as high blood pressure and angina pectoris.

The starting compounds of the general formula II required can be prepared in a manner which is in itself known by Strecker aminonitrile synthesis from compounds of the general formula IV $R^1-NH_2$ (IV)

by reaction with formaldehyde and hydrocyanic acid or sodium cyanide in a suitable solvent, for example water, a compound of the general formula V $R^1-NH-CH_2-CN$ (V)

first being formed and then being converted into the compound II by nitrosation. The nitrosation is carried out in a known manner in a suitable solvent, preferably in water, at temperatures from 0° to 10° C. In this reaction, the nitrous acid is usually produced from an alkali metal nitrite and hydrochloric acid. It is advantageous to adjust the aqueous solution of the compound V to a pH value of 1 to 3 with hydrochloric acid and to add an aqueous solution of the alkali metal nitrite dropwise to the stirred and cooled solution of the compound.

The solution of the resulting compound II can be subjected directly to the cyclisation reaction. However, it is usually appropriate first to take up the nitroso compound II in a suitable organic solvent and to carry out the cyclisation to give the compound of the formula I in this solvent, if appropriate after adding a further solvent.

The compounds of the formula IV are known in some cases, or they can be prepared by the following reactions:

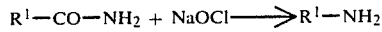

In these reactions, compounds V are first reacted with potassium cyanate VI in a known manner to give the compounds VII, which are in turn converted in a known manner into the compounds IV by oxidation with sodium hypochlorite in a Hoffmann degradation reaction. With the meaning given for $R^1$, the compounds V are amines, the compounds VII are ureas and the compounds IV are hydrazines.

The compounds of the general formula I and their pharmacologically-acceptable acid-addition salts have valuable pharmacological properties.

Their effect on the cardiovascular system is particularly pronounced. Compared with the commercially available compound of similar structure molsidomine, they are effective in lower doses and over a longer period of time. They lower, for example, the blood pressure as well as the pulmonary arterial pressure and the left ventricular enddiastolic pressure, and thus contribute to a relieving of the cardiac action in the sense of an antianginous effect, without thereby provoking reflex tachycardia. They have a lower toxicity than the compounds of similar structure in German Offenlegungsschrift No. 2,930,736.

The compounds of the formula I and their pharmacologically-acceptable acid-addition salts can therefore be administered to humans as drugs by themselves, as mixtures with one another or in the form of pharmaceutical formulations which permit enteral or parenteral administration and contain, as the active constituent, an effective dose of at least one compound of the formula I or of an acid addition salt thereof, in addition to customary pharmaceutically acceptable excipients and additives.

The drugs can be administered orally, for example in the form of pills, tablets, coated tablets, dragees, hard and soft gelatine capsules, solutions, syrups, emulsions or suspensions, or as aerosol mixtures. Administration can, however, also be effected rectally, for example in the form of suppositories, parenterally, for example in the form of injection solutions, or percutaneously, for example in the form of ointments or tinctures.

Pharmaceutically-inert inorganic or organic excipients can be used for preparation of the pharmaceutical products. Pills, tablets, dragees and hard gelatine capsules can be prepared using, for example, lactose, maize starch or derivatives thereof, talc, stearic acid or salts thereof, and the like. Examples of excipients for soft gelatine capsules and suppositories are fats, waxes, semi-solid and liquid polyols, natural or hardened oils and the like. Examples of suitable excipients for the preparation of solutions and syrups are water, sucrose, invert sugar, glucose, polyols and the like. Examples of suitable excipients for the preparation of injection solutions are water, alcohols, glycerol, polyols, vegetable oils and the like.

In addition to the active compounds and excipients, the pharmaceutical products can also contain additives, such as, for example, fillers, extenders, disintegrating agents, binders, lubricants, wetting agents, stabilisers, emulsifiers, preservatives, sweetners, colorants, flavouring or aromatising agents, thickeners, diluents and buffer substances, and also solvents or solubilising agents or agents for achieving a depot effect, as well as salts for modifying the osmotic pressure, coating agents or antioxidants. They can also contain two or more compounds of the formula I or pharmacologically acceptable acid addition salts thereof, as well as other therapeutically active substances.

Examples of such other therapeutically active substances are: $\beta$-blockers, such as, for example, propranolol, pindolol and metoprolol; vasodilators, such as, for example, carbochromene; tranquillisers, such as, for example, barbituric acid derivatives, 1,4-benzodiazepines and meprobamate; diuretics, such as, for example, chlorothiazide; cariac tonics, such as, for example, digitalis products; hypotensive agents, such as, for example, hydralazine, dihydralazine, prazosin, clonidine and Rauwolfia alkaloids; agents which reduce the level of fatty acids in the blood, such as, for example, bezafibrate and fenofibrate; and agents for the prophylaxis of thromboses, such as, for example, phenprocoumon.

The compounds of the formula I, their pharmacologically acceptable acid addition salts and pharmaceutical products which contain the compounds of the formula I or their pharmacologically acceptable acid addition salts as active compounds can be used on humans for combating or preventing illnesses of the cardiovascular system, for example as antihypertensive drugs for various forms of high blood pressure, for combating or preventing agina pectoris, and the like. The dosage can vary within wide limits and is to be adapted to the individual circumstances in each separate case. In general, a daily dose of about 0.5 to 100 mg, preferably 1 to 20 mg, per person, is appropriate in the case of oral administration. Because of the good absorption of the active compounds, the daily dose for other forms of administration is also within a similar range, that is to say in general also 0.5 to 100 mg/person. The daily dose is usually divided into several, for example 2 to 4, part administrations.

To demonstrate the antianginous action of the compounds according to the invention, studies were carried out on mongrel dogs of both sexes under pentobarbital anaesthetic (30 to 40 mg/kg intravenously) or under urethane/chloralose anaesthetic (3 ml/kg of urethane/chloralose mixtures intravenously =20 mg/kg of chloralose and 250 mg/kg of urethane). Respiration of the animals was effected with a Bird Mark 7 respirator. The end expiratory carbon dioxide content (measured with an ultrared absorption recorder) was between 4.5 and 5% by volume. Throughout the entire experiment, the animals under pentobarbital anaesthetic received pentobarbital by continuous intravenous infusion =4 mg (in 6 ml)/kg/h, in order to ensure a constant level of anaesthesia. The animals under urethane/chloralose anaesthesia received no continuous infusion. The infusion was effected through the cephalic vein. After preparation of the experimental animals, a period of about 1 hour was allowed for all the haemodynamic parameters to become established (steady state). The actual experiment was then started.

To determine the mean peripheral blood pressure (=BP), the systolic and diastolic blood pressure were measured peripherally in the femoral artery via a Statham pressure recorder. A Millar tip catheter inserted into the left ventricle via the carotid artery provided the signal for the left ventricular enddiastolic pressure (=LVEDP) and the heart rate (=HR). The mean blood pressure (=PAP) in the pulmonary artery was recorded by a second tip catheter inserted via the jugular vein.

The results obtained are given in the following table:

| Substance | Dose mg/kg | LVEDP $\Delta$mm Hg | PAP $\Delta$mm Hg | BP $\Delta$mm Hg | HR $\Delta$b/min |
|---|---|---|---|---|---|
| A | 0.05 | −2 | −1 | −40 | 0 |
| B | 0.1 | −5 | −5 | −60 | +15 |
| C | 0.01 | −1 | −5 | −25 | +10 |
| D | 0.1 | −4 | −4.5 | −70 | +25 |
| E | 0.01 | −2.5 | −2 | −20 | +10 |
| F | 0.1 | −3 | −6 | −70 | −5 |
| MOL | 0.1 | −2.3 | −1.6 | −18 | +3 |
| ISDN | 0.1 | −3.5 | −2.1 | −6 | +7 |

In the above table:

| | |
|---|---|
| A | = 3-(N—Methyl-N—(tetrahydro-3-thienyl S,S—dioxide)-amino)-sydnonimine hydrochloride |
| B | = 3-(4-Ethoxycarbonylpiperazin-1-yl)-sydnonimine hydrochloride |
| C | = 3-(N—Methyl-N—(tetrahydro-3-thienyl S,S—dioxide)-amino)-$N^6$—(4-nitrobenzoyl)-sydnonimine |
| D | = 3-(N—Methyl-N—(tetrahydro-3-thienyl S,S—dioxide)-amino)-$N^6$—cyclohexylcarbonyl-sydnonimine hydrochloride |
| E | = 3-(4-Ethoxycarbonylpiperazin-1-yl)-$N^6$—cyclohexylcarbonyl-sydnonimine |
| F | = 3-(4-Ethoxycarbonylpiperazin-1-yl)-$N^6$—acetyl-sydnonimine |
| MOL | = Molsidomine (reference substance) |
| ISDN | = Isosorbide dinitrate (reference substance) |
| LVEDP | = Left ventricular enddiastolic pressure |
| PAP | = Mean pulmonary arterial blood pressure |
| BP | = Mean peripheral blood pressure |
| HR | = Heart rate ($\Delta$b/min = beats per minute) |

In the following examples, the percentage data are by weight. Decomp. denotes decomposition.

EXAMPLE 1

3-(N-Methyl-N-(tetrahydro-3-thienyl S,S-dioxide)-amino)-sydnonimine hydrochloride.

20.5 g of 1-methyl-1-(tetrahydro-3-thienyl S,S-dioxide)-hydrazine hydrochloride are dissolved in 120 g of water. A solution of 4.9 g of sodium cyanide in 10 ml of water is added dropwise at 0° to 5° C., and 8.3 ml of 40% strength formalin solution are subsequently added dropwise, also at 0° to 5° C. The reaction mixture is then allowed to warm to room temperature and is stirred for a further 15 hours and then cooled to 0° to 5° C. and adjusted to a pH value of 1 to 2 with about 8 ml of concentrated hydrochloric acid. 6.9 g of sodium nitrite are dissolved in 15 ml of water and the solution is added dropwise at 0° to 5° C., whereupon an oil separates out. This oil is extracted by shaking with ethyl acetate (100 ml), and the organic phase is dried over sodium sulphate. After adding 100 ml of methanol, a total of about 70 to 80 g of hydrogen chloride are passed in at 5° to 10° C. in the course of 2 to 3 hours. The mixture is now cooled to 0° C. and is subsequently stirred for 2 hours, and the product is filtered off with suction and recrystallised from an isopropanol/water mixture: melting point=177° to 179° C., yield: 8.3 g (35% of theory).

The cyclisation proceeds in a similar manner if sulphuric acid, nitric acid, phosphoric acid or trifluoroacetic acid is used instead of hydrogen chloride, and/or if the cyclisation is carried out at temperatures from 0° to 40° C., and/or if the methanol is replaced by a corresponding amount of ethyl acetate, ethanol, i-propanol, n-propanol, i-butanol or n-butanol.

EXAMPLE 2

3-(4-Ethoxycarbonylpiperazin-1-yl)-sydnonimine hydrochloride.

21 g of 1-ethoxycarbonyl-4-aminopiperazine hydrochloride are dissolved in 120 ml of water. A solution f 4.9 g of sodium cyanide in 10 ml of water is then added dropwise at a temperature of 0° to 5° C., and 8.3 ml of 40% strength formalin solution are subsequently added dropwise, also at 0° to 5° C. The mixture is then allowed to warm to room temperature and is stirred for a further 15 hours, cooled to 0° to 5° C. and adjusted to a pH value of 1 to 2 with about 8 ml of concentrated hydrochloric acid. 6.9 g of sodium nitrite are dissolved in 15 ml of water and the solution is added dropwise at 0° to 5° C., whereupon an oil separates out. This oil is extracted by shaking with ethyl acetate (100 ml), and the organic phase is dried over sodium sulphate. After adding 100 ml of methanol, a total of about 70 to 80 g of hydrogen chloride are passed in at 5° to 10° C. in the course of 2 to 3 hours. The mixture is now cooled to 0° C. and is subsequently stirred for 2 hours and the product is filtered off with suction and recrystallised from isopropanol: melting point=170° to 171° C., yield: 12.6 g (45% of theory).

The cyclisation proceeds in a similar manner if sulphuric acid, nitric acid, phosphoric acid or trifluoroacetic acid is used instead of hydrogen chloride and/or the cyclisation is carried out at temperatures from 0° to 40° C., and/or the methanol is replaced by a corresponding amount of ethyl acetate, ethanol, i-propanol, n-propanol, i-butanol or n-butanol.

EXAMPLE 3

3-(N-Methyl-N-(tetrahydro-3-thienyl S,S-dioxide)-amino)-$N^6$-ethoxycarbonyl-sydnonimine.

5.4 g of 3-(N-methyl-N-(tetrahydro-3-thienyl S,S-dioxide)-amino)-sydnonimine hydrochloride and 4.2 g of sodium bicarbonate are dissolved in 50 ml of water and the solution is combined with a solution of 3.25 g of ethyl chloroformate in 50 ml of methylene chloride. After the mixture has been stirred at room temperature for 24 hours, it is filtered off with suction, the methylene chloride phase is concentrated and the residue is combined with the solid filtered off and is recrystallised from 30 ml of methanol: melting point=139° to 142° C., yield: 2.3 g (38% of theory).

The following compounds can be synthesised analogously to this example, the solvent and reaction temperature used for the acylation being given after the melting point:

3-(N-methyl-N-(tetrahydro-3-thienyl S,S-dioxide)-amino)-$N^6$-benzoyl sydnonimine; melting point=152° to 153° C., in water/methylene chloride at 10° C., 3-(N-methyl-N-(tetrahydro-3-thienyl S,S-dioxide)-amino)-$N^6$-(4-nitrobenzoyl)-sydnonimine; melting point=221° to 222° C. (decomp.), in water/methylene chloride at 20° C., 3-(N-methyl-N-(tetrahydro-3-thienyl S,S-dioxide)-amino)-$N^6$-cyclohexylcarbonyl-sydnonimine hydrochloride; melting point=150° C. (decomp.), in water at 0° C., 3-(N-methyl-N-(tetrahydro-3-thienyl S,S-dioxide)-amino)-$N^6$-(4-methylbenzoyl)-sydnonimine; melting point=146° to 149° C., in water/methylene chloride at 20° C., 3-(4-ethoxycarbonylpiperazin-1-yl)-$N^6$-ethoxycarbonyl-sydnonimine; melting point=170° to 172° C., in water at 20° C., 3-(4-ethoxycarbonylpiperazin-1-yl)-$N^6$-cyclohexylcarbonyl-sydnonimine; melting point=136° to 137° C., in water at 0° C., 3-(4-ethoxycarbonylpiperazine-1-yl)-$N^6$-benzoyl-sydnonimine; melting point=159° to 160° C., in water/methylene chloride at 25° C., 3-(4-ethoxycarbonylpiperazin-yl)-$N^6$-(ethoxycarbonylcarbonyl)sydnonimine; melting point=123° to 124° C., in water/methylene chloride at 0° C., 3-(4-ethoxycarbonylpiperazin-1-yl)-$N^6$-(4-chlorobenzoyl)-sydnonimine; melting point=203° to 207° C. (decomp.), in water/methylene chloride at 20° C., 3-(4-ethoxycarbonylpiperazin-1-yl)-$N^6$-pivaloyl-sydnonimine; melting point=151° to 152° C., in water at 10° C., 3-(4-ethoxycarbonylpiperazin-1-yl)-$N^6$-(1-adamantylcarbonyl)-sydnonimine; melting point=215° to 216° C., in water/methylene chloride at 20° c., 3-(4-ethoxycarbonylpiperazin-1-yl)-$N^6$-(3-[-]-pinylcarbonyl)-sydnonimine; melting point=145° to 146° C., in water/methylene chloride at 20° C., 3-(N-methyl-N-(tetrahydro-3-thienyl S,S-dioxide)-amino)-amino)-$N^6$-(4-methoxybenzoyl)-sydnonimine; melting point=140° to 143° C., in dimethylformamide at 10° C., 3-(N-ethyl-N-ethyl-N-(tetrahydro-3-thienyl S,S-dioxide)-amino)-$N^6$-methoxycarbonyl-sydnonimine; melting point=140° to 143° C., in water at 0° C., 3-(N-methyl-N-(tetrahydro-3-thienyl S,S-dioxide)-amino)-N⁶-(4-chlorobenzoyl)-sydnonimine; melting point=141° to 143° C., in water/methylene chloride at 20° C., 3-(N-methyl-N-(tetrahydro-3-thienyl S,S-dioxide)-amino)-N⁶-pivaloyl-sydnonimine; melting point=160° to 162° C., in water at 10° C., 3-N-(methyl-N-(tetrahydro-3-thienyl S,S-dioxide)-amino)-N⁶-ethoxycarbonylcarbonyl-sydnonimine; melting point 147° to 150° C., in water/methylene chloride at 0° C., 3-(4-ethoxycarbonylpiperazin-1-yl)-N⁶-methoxycarbonyl-sydnonimine; melting point 181° to 183° C., in water at 0° C., 3-(4-ethoxycarbonylpiperazin-1-yl)-N⁶-(4-methylbenzoyl)-sydnonimine; melting point 165° to 166° C., in water/methylene chloride at 20° C., and 3-(4-ethoxycarbonylpiperazin-1-yl)-N⁶-(4-nitrobenzoyl)-sydnonimine; melting point 210° to 212° C., in water/methylene chloride at 20° C.

EXAMPLE 4

3-(4-Ethoxycarbonylpiperazin-1-yl)-N⁶-acetyl-sydnonimine.

5.6 g of 3-(4-ethoxycarbonylpiperazin-1-yl)-sydnonimine hydrochloride are stirred in a mixture of 20 ml of acetic anhydride and 20 ml of absolute pyridine at room temperature for 14 hours. The precipitate is filtered off with suction and rinsed with methylene chloride, melting point=164° to 165° C.; yield: 3.5 g (62% of theory).

The following compounds can be synthesised analogously to this example, the acylating agent and reaction temperature used for the acylation being given after the melting point:

3-(N-methyl-N-(tetrahydro-3-thienyl S,S-dioxide)-amino-N⁶-methoxyacetyl-sydnonimine; melting point=151° to 153° C., in methoxyacetic anhydride/pyridine at 20° C., 3-(N-ethyl-N-(tetrahydro-3-thienyl S,S-dioxide)-amino)-N⁶-acetylsydnonimine; melting point=162° to 164° C. in acetic anhydride at 5° C., 3-(4-methoxycarbonylpiperazin-1-yl)-N⁶-acetyl-sydnonimine; melting point=188° to 191° C., in acetic anhydride at 50° C., and 3-(4-methoxycarbonylpiperazin-1-yl)-N⁶-methoxyacetyl-sydnonimine; melting point=148° to 151° C. in methoxyacetic anhydride/pyridine at 40° C.

Pharmaceutical products are described in the following examples.

EXAMPLE 5

Soft gelatine capsules containing 5 mg of active compound per capsule:

|  | Per capsule |
| --- | --- |
| 3-(N—Methyl-N—(tetrahydro-3-thienyl S,S—dioxide)-amino)-sydnonimine | 5 mg |
| Triglyceride mixture fractionated from coconut oil | 150 mg |
| Capsule contents | 155 mg |

EXAMPLE 6

Injection solution containing 1 mg of active compound per ml:

|  | Per ml |
| --- | --- |
| 3-(N—Methyl-N—(tetrahydro-3-thienyl S,S—dioxide)-amino)-sydnonimine hydrochloride | 1.0 mg |
| Polyethylene glycol 400 | 0.3 ml |
| Sodium chloride | 2.7 mg |
| Water for injection purposes | to 1 ml |

EXAMPLE 7

Emulsions containing 3 mg of active compound per 5 ml:

|  | Per 100 ml of emulsion |
| --- | --- |
| 3-(4-Ethoxycarbonylpiperazin-1-yl)-sydnonimine hydrochloride | 0.06 g |
| Neutral oil | q.s. |
| Sodium carboxymethylcellulose | 0.6 g |
| Polyoxyethylene stearate | q.s. |
| Pure glycerol | 0.2 to 2.0 g |
| Flavour substance | q.s. |
| Water (demineralised or distilled) | to 100 ml |

EXAMPLE 8

Rectal drug form containing 4 mg of active compound per suppository:

|  | Per suppository |
| --- | --- |
| 3-(4-Ethoxycarbonylpiperazin-1-yl)-sydnonimine | 4 mg |
| Suppository base | to 2 g |

EXAMPLE 9

Tablets containing 2 mg of active compound per tablet:

|  | Per tablet |
| --- | --- |
| 3-(N—Methyl-N—(tetrahydro-3-thienyl S,S—dioxide)-amino)-N⁶—benzoyl-sydnonimine lactate (finely ground) | 2 mg |
| Maize starch (white) | 150 mg |
| Lactose | 60 mg |
| Microcrystalline cellulose | 50 mg |
| Polyvinylpyrrolidone | 20 mg |
| Magnesium stearate | 2 mg |
| Sodium carboxymethyl-starch | 25 mg |
|  | 309 mg |

What is claimed is:

1. A pharmacologically-active compound which, in free-base state, is of the formula $$R^2-N=\underset{\oplus}{\overset{O-N}{\underset{\phantom{x}}{\bigcirc}}}-N-N\underset{\phantom{x}}{\overset{\phantom{x}}{\bigcirc}}N-\overset{O}{\underset{\phantom{x}}{\overset{\|}{C}}}-O-R^3$$

wherein $R^2$ is —H or —CO—$R^4$;

$R^3$ is methyl, ethyl, propyl or isopropyl;

$R^4$ is aliphatic hydrocarbyl with from 1 to 4 carbon atoms and optionally substituted by alkoxy with from 1 to 3 carbon atoms, cycloaliphatic hydrocarbyl with from 5 to 7 ring carbon atoms, bicycloaliphatic hydrocarbyl with from 7 to 14 ring carbon atoms, tricycloaliphatic hydrocarbyl with from 7 to 16 ring carbon atoms, alkoxy with from 1 to 6 carbon atoms, carbocyclic aryloxy with from 6 to 12 ring carbon atoms, alkoxycarbonyl with from 2 to 7 carbon atoms, carbocyclic aryl with from 6 to 12 ring carbon atoms or such aryl with from 1 to 3 substituents each of which is a member selected from the group consisting of halo, alkyl with from 1 to 3 carbon atoms, alkoxy with from 1 to 3 carbon atoms and nitro, and at most 2 of which are nitro.

2. A compound according to claim 1 wherein $R^2$ is —H.

3. A compound according to claim 1 wherein $R^2$ is —CO—$R^4$.

4. A compound according to claim 3 wherein $R^4$ is aliphatic hydrocarbyl.

5. A compound according to claim 3 wherein $R^4$ is alkoxysubstituted aliphatic hydrocarbyl.

6. A compound according to claim 3 wherein $R^4$ is cycloaliphatic hydrocarbyl.

7. A compound according to claim 6 wherein $R^4$ is cyclohexyl.

8. A pharmacologically-active compound according to claim 1 wherein $R^4$ is aliphatic hydrocarbyl with from 1 to 4 carbon atoms and optionally substituted by alkoxy with from 1 to 3 carbon atoms, cyclohexyl, pinyl, adamantyl, alkoxy with from 1 to 6 carbon atoms, phenoxy, alkoxycarbonyl with 2 to 3 carbon atoms, phenyl, nitrophenyl, methylphenyl, methoxyphenyl or chlorophenyl.

9. A compound according to claim 3 wherein $R^4$ is alkoxy.

10. A compound according to claim 3 wherein $R^4$ is alkoxycarbonyl.

11. A compound according to claim 10 wherein $R^4$ is methoxycarbonyl or ethoxycarbonyl.

12. A compound according to claim 3 wherein $R^4$ is carbocyclic aryl.

13. A compound according to claim 12 wherein $R^4$ is phenyl.

14. A compound according to claim 3 wherein $R^4$ is substituted carbocyclic aryl.

15. A compound according to claim 14 wherein $R^4$ is substituted phenyl.

16. A compound according to claim 1 which is a pharmacologically-acceptable acid-addition salt.

17. A compound according to claim 1 wherein
$R^3$ is methyl or ethyl, and
$R^4$ is alkyl with from 1 to 4 carbon atoms, methoxymethyl, cycloalkyl with from 5 to 7 ring carbon atoms, 2,6,6-trimethyl-bicyclo[3.1.1]heptyl, tricyclo[3.3.1.1$^{3,7}$]decyl, methoxy, ethoxy, phenoxy, ethoxycarbonyl, phenyl, tolyl, nitrophenyl or chlorophenyl.

18. A compound according to claim 17 wherein $R^4$ is alkyl with from 1 to 4 carbon atoms, methoxymethyl, cyclohexyl, 2,6,6-trimethyl-bicyclo[3.1.1]heptyl, tricyclo[3.3.1.1$^{3,7}$]decyl, methoxy, ethoxy, phenoxy, ethoxycarbonyl, phenyl, tolyl, nitrophenyl or chlorophenyl.

19. A compound according to claim 17 wherein $R^4$ denotes methyl, ethyl, cyclohexyl, phenyl, 4-chlorophenyl or 4-nitrophenyl.

20. A compound according to claim 1 which is 3-(4-ethoxycarbonylpiperazin-1-yl)sydnonimine or a physiologically-acceptable acid-addition salt thereof.

21. A compound according to claim 1 which is 3-(4-ethoxy-carbonylpiperazin-1-yl)-$N^6$-cyclohexylcarbonylsydnonimine or a physiologically-acceptable acid-addition salt thereof.

22. A compound according to claim 1 which is 3-(4-ethoxycarbonylpiperazin-1-yl)-$N^6$-acetylsydnonimine or a physiologically-acceptable acid-addition salt thereof.

23. A compound according to claim 1 wherein aliphatic hydrocarbyl in the definition of $R^4$ has from 1 to 4 carbon atoms and is either unsubstituted or monosubstituted by alkoxy with from 1 to 3 carbon atoms.

24. A process for prophylaxis for or treatment of cardiovascular illness which comprises administering an effective amount of a pharmacologically-acceptable compound according to claim 1 to a subject prone to or afflicted with such illness.

25. A medicament composition which is useful for prophylaxis for or treatment of cardiovascular illness and which comprises pharmaceutically-acceptable excipient and/or additive and an effective amount, per unit dose, of a compound according to claim 1.

* * * * *